US005782879A

United States Patent [19]
Rosborough et al.

[11] Patent Number: 5,782,879
[45] Date of Patent: Jul. 21, 1998

[54] APPARATUS AND METHOD FOR DISCRIMINATING FLOW OF BLOOD IN A CARDIOVASCULAR SYSTEM

[75] Inventors: John P. Rosborough, Houston; M. Zafar A. Munshi, Missouri City; Chris A. Bonnerup, Houston, all of Tex.

[73] Assignee: Sulzer Intermedics Inc., Angleton, Tex.

[21] Appl. No.: 458,952

[22] Filed: Jun. 2, 1995

[51] Int. Cl.⁶ ................................................ A61N 1/39
[52] U.S. Cl. .............................. 607/6; 607/5; 600/504
[58] Field of Search .................................. 128/691–693, 128/713, 734; 607/6, 18, 24, 5, 17, 23; 600/526, 547, 504–506

[56] References Cited

U.S. PATENT DOCUMENTS

| | | |
|---|---|---|
| 3,450,984 | 6/1969 | Holmes . |
| 4,291,699 | 9/1981 | Geddes et al. ................. 607/6 |
| 4,450,527 | 5/1984 | Sramek ........................ 128/734 |
| 4,884,576 | 12/1989 | Alt . |
| 4,905,696 | 3/1990 | Amundson et al. . |
| 4,919,136 | 4/1990 | Alt . |
| 4,967,748 | 11/1990 | Cohen . |
| 5,003,976 | 4/1991 | Alt . |
| 5,085,213 | 2/1992 | Cohen . |
| 5,146,414 | 9/1992 | McKown et al. ............. 128/713 |
| 5,174,299 | 12/1992 | Nelson . |
| 5,188,106 | 2/1993 | Nappholz et al. . |
| 5,213,098 | 5/1993 | Bennett et al. . |
| 5,243,976 | 9/1993 | Ferek-Petric et al. ......... 607/6 |
| 5,271,408 | 12/1993 | Breyer et al. . |
| 5,316,001 | 5/1994 | Ferek-Petric et al. . |
| 5,318,595 | 6/1994 | Ferek-Petric et al. ........ 607/17 |
| 5,344,430 | 9/1994 | Berg et al. .................. 128/734 |
| 5,385,576 | 1/1995 | Noren et al. ................ 182/734 |
| 5,409,009 | 4/1995 | Olson . |
| 5,441,521 | 8/1995 | Hedberg ....................... 607/6 |
| 5,497,780 | 3/1996 | Zehender ...................... 607/17 |
| 5,529,072 | 6/1996 | Sramek ........................ 128/693 |
| 5,602,342 | 2/1997 | Strandberg .................. 128/691 |

FOREIGN PATENT DOCUMENTS

| | | |
|---|---|---|
| 0310026 | 4/1989 | European Pat. Off. . |
| 0347708 | 12/1989 | European Pat. Off. . |
| 0474958 | 3/1992 | European Pat. Off. . |
| 0541338 | 3/1992 | European Pat. Off. ........ 607/18 |
| 0620420 | 5/1994 | European Pat. Off. . |
| 0620420 | 10/1994 | European Pat. Off. . |
| 0634192 | 1/1995 | European Pat. Off. . |
| 8901803 | 3/1989 | WIPO . |

OTHER PUBLICATIONS

M. Manz et al., Erroneous Discharge from an Implanted Automatic Defibrillator During Supraventricular Tachyarrhythmia Induced Ventricular Fibrillation, *The American Journal of Cardiology*, vol. 57, Feb. 1, 1986, pp. 343–344.

W. Kaltenbrunner et al., Induction of Life–threatening Ventricular Tachyarrhythmias by Serial Inappropriate AICD–pulsing in the Hyperthyroid State, *Journal of Electrophysiology*, vol. 1, No. 4, 1987, pp. 320–325.

(List continued on next page.)

*Primary Examiner*—William E. Kamm
*Assistant Examiner*—George R. Evanisko
*Attorney, Agent, or Firm*—John R. Merkling; Richard L. Robinson

[57] ABSTRACT

An implantable cardiac stimulator delivers a first electrical shock via implantable stimulating electrodes at a time when there is substantially no flow of blood. At least one of the stimulating electrodes is disposed in a blood flow path of the cardiovascular system. The first shock is of insufficient energy level to cause defibrillation. An electrical potential is measured as a function of time between the blood-contacting electrode and a reference electrode following delivery of the first shock to obtain a first potential equilibration function under no-flow conditions. A second therapeutic electrical shock, of sufficient energy level to effect defibrillation, is delivered via the stimulating electrodes. A second potential equilibration function is measured following delivery of the second shock. The first and second potential equilibration functions are compared, and if the two functions are sufficiently different in morphology, it is determined that blood is flowing.

22 Claims, 10 Drawing Sheets

OTHER PUBLICATIONS

T. Cohen et al., A Hemodynamically Responsive Antitachycardia System: Theoretical Bases for Design, Journal of Electrophysiology, vol. 2, No. 4, 1988, pp. 352–357.

D. Khoury et al., Continuous Right Ventricular Volumn Assessment by Catheter Measurement of Impedence for Antitachycardia System Control, PACE, vol. 12, Dec. 1989, pp. 1918–1926.

A. Sharma et al., Right Ventricular Pressure During Ventricular Arrhythmias in Humans: Potential Implications for Implantable Antitachycardia Devices, J. Am Coll Cardiol, vol. 15, No. 3, Mar. 1, 1990, pp. 648–655.

K. Ellenbogen et al., Usefulness of Right Ventricular Pulse Pressure As a Potential Sensor for Hemodynamically Unstable Ventricular Tachycardia, The American Journal of Cardiology, vol. 65, May 1, 1990, pp. 1105–1111.

T. Cohen et al., Mixed Venous Oxygen Saturation for Differentiating Stable from Unstable Tachycardias, American Heart Journal, vol. 122, No. 3, Part 1, Sep. 1991, pp. 733–740.

M. Hiles et al., Detection of Ventricular Tachycardia and Fibrillation Using Coronary Sinus Blood Temperature: A Feasibility Study, PACE, vol. 16, Dec. 1993, pp. 2266–2278.

D. Buerk, Biosensors Theory and Applications, Technomic Publishing Co., Inc., Lancaster, PA, U.S.A., Ch. 1, pp. 1–19.

T. Cohen et al., Biosensors: Use in Future Implantable Cardioverter–Defibrillators, Ch. 23, Implantable Cardioverter–Defibrillators, Blackwell Scientific Pub., Oxford, 1993, pp. 397–412.

APPARATUS AND METHOD FOR DISCRIMINATING FLOW OF BLOOD IN A CARDIOVASCULAR SYSTEM

BACKGROUND OF THE INVENTION

1. Field of the Invention

The present invention relates generally to devices and methods for discriminating flow of blood in a cardiovascular system, and more particularly to such devices and methods for use in combination with implantable cardiac stimulators such as automatic implantable cardioverter-defibrillators, either with or without bradycardia pacing capabilities.

2. Background of the Art

Hemodynamically unstable cardiac arrhythmias, such as ventricular fibrillation, render the heart ineffective as a blood pump and can result in sudden death. For those patients who are susceptible to recurrent ventricular fibrillation, an important prophylactic measure against sudden death is provided by the automatic implantable cardioverter-defibrillator (AICD). The AICD diagnoses fibrillation upon occurrence, and automatically provides appropriate therapy to defibrillate the heart. Therapy to terminate the fibrillation can include delivering high-energy defibrillation shocks between a pair of electrodes, each of which is implanted either within a chamber of the heart or a lumen of the cardiovascular system, or elsewhere in the vicinity of the heart. Ideally, an AICD should assess the hemodynamic condition of the patient as part of the diagnostic function, and deliver an appropriate therapy only when needed.

Discerning the hemodynamic condition of the patient presents a particular challenge where the AICD device relies on intracardiac electrogram (IEGM) signals for diagnostic purposes. Presently available AICDs sense IEGM signals via sensing electrodes placed in the right ventricle and/or the right atrium. Sense amplifiers and other circuitry in the AICD are connected to the sensing electrodes to receive and detect the IEGM signals resulting from ventricular depolarization and repolarization. Typically, the sensed signal includes a QRS depolarization signal followed by a T-wave repolarization signal. Various algorithms, such as R—R interval timing, epicardial conduction time differences (ECTD), and probability density functions, are used to analyze the sensed signal and diagnose arrhythmias. The detected amplitude of the IEGM signals for a given patient can vary significantly due to a number of factors, including the presence of therapeutic drugs, whether the sensing electrode is in an acute or chronic phase of implantation, occurrence of myocardial infarction, post-shock alterations of the electrical activity of the myocardium, and post-shock alterations of the electrochemical surface activity of the sensing electrode. The latter two factors are particularly important because the alterations of the electrical activities of the patient's heart or electrochemical characteristics of the sensing electrode occur at a critical time, i.e., after automatic delivery of shock therapy to a patient who has been diagnosed by the AICD to be in a state of ventricular fibrillation.

Errors in detection of the IEGM signals during the critical post-shock period can adversely affect the ability of the AICD to provide further therapy, or refrain from providing therapy, as may be appropriate. In some cases, defibrillation therapy may have been successful but that success is not confirmed by the AICD due to difficulties in accurately sensing the post-shock electrical activities of the heart, resulting in the AICD delivering additional unnecessary therapy. Such misapplied therapies could cause discomfort to the patient and/or compromise the efficacy of previously applied therapy by causing myocyte stunning, which deleteriously affects the ability of cardiac muscle tissue to contract. Unnecessary therapy also could adversely affect the functioning of the AICD in the future. Delivery of excess shocks depletes the battery prematurely and thereby reduces the longevity of the device. A plurality of shocks delivered in rapid succession also places greater stress on the battery than the same number of shocks delivered at widely spaced intervals, and can cause a permanent reduction in the current capacity of the battery, resulting in a lengthening of the time required to charge the capacitors in the future. In other cases, the AICD may sense electrical activity of the heart that appears to indicate cardiac systole, but nevertheless the heart is in a state of mechanical asystole and is not pumping blood. This phenomenon, called electromechanical dissociation or passive electrical activity, may cause the AICD to forego delivery of additional necessary therapy. Backup bradycardia pacing is provided in the present generation of AICDs to prevent death due to asystole following termination of ventricular fibrillation. The AICD is still dependent, however, upon its interpretation of the intracardiac electrogram signal to determine that backup pacing is necessary. Hence, there is a crucial need for a flow sensing means that can be used in combination with an AICD that can detect whether blood is flowing following delivery of defibrillation therapy, independently of the intracardiac electrogram signal, so that therapy either can be continued or discontinued, as appropriate.

Various biosensors have been proposed for use in combination with implantable cardioverter-defibrillators and other cardiac stimulating devices to detect biological parameters other than IEGM signals. Examples of parameters that have been investigated are: blood pressure, blood oxygen saturation, cardiac impedance, blood pH, blood temperature, patient activity, motion and position, respiratory rate, and blood velocity. The ultimate purpose of sensing any of the above-listed parameters is to discern the flow of blood in the cardiovascular system, but it should be recognized that none of the listed parameters, except blood velocity, is a direct indication of blood flow. The listed parameters other than blood velocity are merely correlated with the flow of blood, and the degree of correlation is not necessarily sufficiently high and sufficiently consistent to be clinically useful. Even those parameters that show a high degree of correlation with blood flow can be difficult to exploit in a practical device because special sensing elements may be required that must be located on a lead or catheter disposed within the cardiovascular system. Such special sensing elements may be unacceptably bulky or insufficiently reliable. Ideally, the parameter to be sensed should be one that is directly indicative of the flow of blood and can be sensed without using special sensing elements.

SUMMARY OF THE INVENTION

A design goal in the development of new cardioverter-defibrillator devices has been to incorporate the ability to sense flow of blood without requiring special leads or special sensor elements. The present invention is believed to enable that goal to be reached. We have invented an apparatus and method for discriminating flow of blood that can be implemented in an AICD using only electrodes that are already used with the AICD for other purposes.

In accordance with one aspect of the present invention, a flow of blood is discriminated in a cardiovascular system via an electrode disposed in a blood flow path of the cardiovascular system and wherein an electrical potential is imposed on the electrode. The electrical potential on the electrode is then allowed to discharge at least partially. As it discharges, the electrical potential is sensed in the time domain. The sensed electrical potential is analyzed to discriminate flow of blood.

It is an object of the present invention to provide an apparatus and method for discriminating flow of blood in a cardiovascular system.

Other objects and advantages of the present invention will be apparent to those of ordinary skill in the art from the following description of the preferred embodiments of and modes of carrying out the invention, made with reference to the attached figures.

DETAILED DESCRIPTION OF THE PREFERRED EMBODIMENTS

Figure 1:
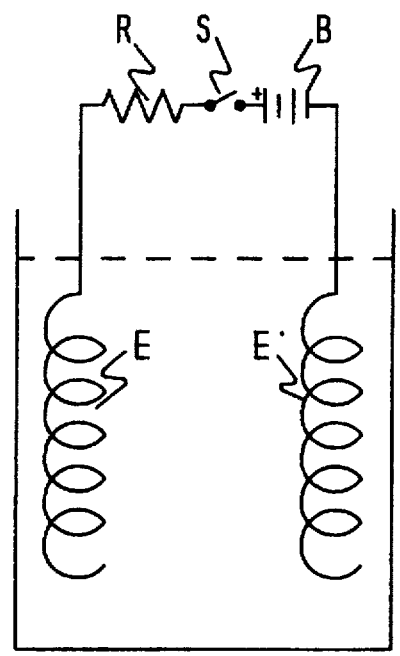
FIG. 1 is a schematic representation of an electrolyte circuit useful for understanding an underlying principle of the invention.

A preferred mode of carrying out the present invention involves an automatic implantable cardioverter\defibrillator (AICD) that includes means for sensing flow of blood in the cardiovascular system. The flow sensing means includes a first electrode that is adapted to be placed in a path of flow of blood within the cardiovascular system. The AICD is arranged to impose an electrical potential upon the first electrode relative to a second electrode, which second electrode can be placed in a path of flow of the blood within the cardiovascular system, or can be placed subcutaneously, or can be placed elsewhere in the body, provided that an ionically conductive electrical path exists through the body between the first electrode and the second electrode. The AICD is also arranged to permit sensing of the electrical potential of the first electrode relative to a reference electrode, which reference electrode can be the above-mentioned second electrode or can be a third electrode, provided that an ionically conductive electrical path exists through the body between the first electrode and the third electrode. The conventional stimulating and/or sensing electrodes that are already located on leads used with presently available AICDs can also function as the first, second and reference electrodes of the present invention, thereby avoiding the need for special leads or electrodes.

In accordance with the present invention, flow of blood is discriminated by imposing an electrical potential upon the first electrode located in a blood flow path of the cardiovascular system, allowing the electrical potential of the first electrode to discharge (at least partially) over time through the conductive ionic path, and sensing and analyzing the discharging electrical potential of the first electrode in the time domain. We have discovered that the morphology of the discharging electrical potential waveform sensed at the first electrode is distinguishably different under flow and non-flow conditions, and that algorithms can be generated that, when applied to the sensed waveform, are capable of discriminating flow of blood in the vicinity of the first electrode.

Although we do not wish the invention to be bound by or limited to any particular theory of operation, we believe that the electrochemical phenomenon described below underlies our discovery and is useful in understanding the invention. The residual electrical potential at the first electrode following termination of the imposed potential is believed to be the result of a complex phenomenon involving the generation of a concentration gradient of charged ionic species in the vicinity of the electrode-to-electrolyte interface. In this context, the electrolyte is understood to be blood and its constituent components, including water and various dissolved salts. The concentration gradient arises from oxidation and reduction reactions that occur at the electrode-to-electrolyte interface, causing a local diminution in the concentration of reactant ionic species relative to the concentration in the bulk of the electrolyte. The concentration gradient also arises from migration of charged species in response to the electric field imposed between the first and second electrodes. Following termination of the imposed potential, the concentration gradient will equilibrate over time due to diffusion of ions and neutral molecules. The region adjacent the electrode surface in which the concentration gradient is developed is also called the diffusion layer. The thickness of the diffusion layer can vary greatly, but for the sake of relative comparisons, may be regarded as being on the order of about one millimeter. The rate of diffusion of species across the diffusion layer is proportional to the concentration gradient and to a diffusion constant, and inversely proportional to the thickness of the diffusion layer. The residual potential of the first electrode decays logarithmically as a function of time as the concentration gradient equilibrates, provided that the electrolyte in the vicinity of the first electrode is quiescent. Flow of electrolyte, i.e., blood, in the vicinity of the electrode-to-electrolyte interface effectively reduces the thickness of the concentration gradient by convectively replenishing depleted species in the region of the electrode. Convection is negligible in the portions of the diffusion layer nearest the electrode, due to frictional forces between the electrode and the solution, but convective transport in the outermost portions of the diffusion layer is significant. Thus, the overall thickness of the diffusion layer is reduced, thereby increasing the rate of diffusion. The result is a generally more rapid equilibration of the potential of the first electrode relative to the bulk of the electrolyte, and hence relative to the reference electrode. Complex flow patterns may also result in a non-logarithmic morphology of the electrode potential waveform. The discernible difference in the potential equilibration function of the first electrode attributable to electrolyte convection is exploited by the present invention to discriminate flow of blood. In the context of the preferred embodiment, the subject phenomenon arises from a discharge of electrical energy, such as a defibrillation shock, from a charged high-voltage storage capacitor in an AICD. The electrical energy is discharged between an electrode pair, one of which comprises the first electrode discussed above and the other of which comprises the second electrode.

Figure 2:
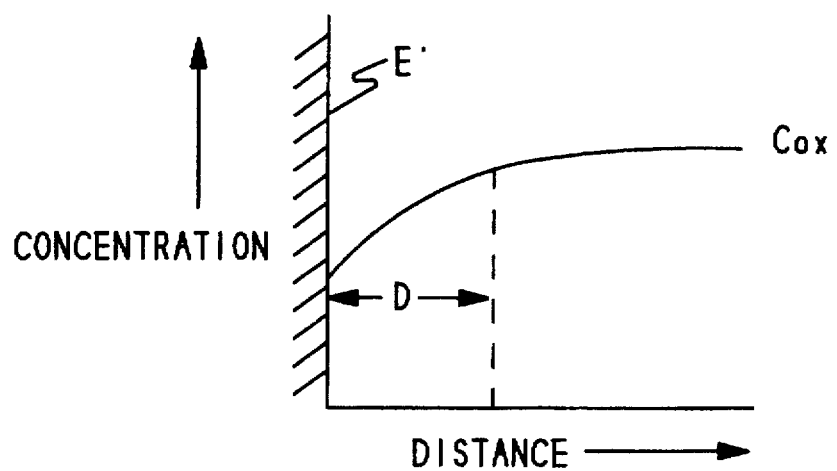
FIG. 2 is a graph showing a concentration gradient of an oxidant species in the electrolyte in the vicinity of an electrode of the circuit of FIG. 1.

We believe that the phenomenon can be readily understood with reference to FIGS. 1 and 2 by considering the case of two electrodes E and E' immersed in an aqueous electrolyte solution, such as a salt solution, with each electrode connected externally to opposite terminals of a direct current power supply, such as a battery B, through a current-limiting resistor R. The external circuit can be broken or completed with switch S. When the switch S is open, no current flows between the two electrodes E and E'. There is no net electron transfer across the electrode-to-electrolyte interface, and potential equilibrium between electrodes E and E' is established.

As switch S is closed, battery B imposes a potential differential between the two electrodes, resulting in electrode E' becoming more negative and electrode E becoming more positive. Oxidation reactions take place at the cathode E' and reduction reactions take place at the anode E, resulting in a net flow of current through the electrolyte. The resulting potential difference between electrodes E and E' depends (apart from the voltage and resistance characteristics of battery B, and the resistance of resistor R) upon a resistance component attributable to the resistance of the bulk electrolyte (and, in some cases, to the resistance of an adherent layer of reaction product on the surface of the electrode), and to an overvoltage component attributable to changes in concentration of ionic species in the vicinity of the electrodes due to electrochemical reactions occurring there. The concentration overvoltage is also partly attributable to the electric field between electrodes E and E' that influences the movement of ionic species in the electrolyte.

Concentration overvoltage may be further understood by considering the following process with reference to FIG. 2:

$$C_{Ox} + ne^- \rightleftharpoons C_{Red}$$

where $C_{Ox}$ is the oxidized chemical species, $C_{Red}$ is the reduced chemical species, $e^-$ is the electronic charge, and n is the number of electrons exchanged in the reaction process. In the electrochemical process, ions are depleted or accumulated at the electrode-to-electrolyte interface, causing changes in concentration in the diffusion layer D. At the cathode, oxidation occurs at a faster rate than reduction. At the anode, reduction occurs at a faster rate than oxidation. The concentration of $C_{Ox}$ close to the cathode surface is less than the concentration of $C_{Ox}$ in the bulk. Likewise, the concentration of $C_{Red}$ close to the anode surface is less than the concentration of $C_{Red}$ in the bulk. Thus, a concentration gradient is set up across the diffusion layer D, resulting in a concentration overvoltage. Mass transfer takes place by diffusion across the diffusion layer.

When the switch S is opened again, the potential between the two electrodes equilibrates due to diffusion of charged species across the diffusion layer, such that concentration equilibrium is re-established. The transient response of the concentration overvoltage is relatively slow on interruption of current, and decays at a rate related to the diffusion coefficients of the reactive species involved, and to the thickness of the diffusion layer generated, where the electrolyte solution is quiescent. Stirring of the electrolyte solution or rotation or vibration of the electrode results in convective transport of the reactive species to the vicinity of the electrode, thereby reducing the effective thickness of the diffusion layer and causing the rate of decay of the concentration overvoltage to be generally more rapid.

Generally, the potential equilibration following current interruption is logarithmic as a function of time. Depending upon the type of electrode, the nature of the ionic species in the electrolyte, and the extent of the concentration gradient, voltage recovery to equilibrium could require a few seconds to several hours. The rate of recovery is inversely related to the magnitude of the current that was flowing through the electrode. If the current was small, the diffusion layer generated would be relatively thin and the rate of recovery would be rapid. If the current was very large, i.e., as in the case of a therapeutic defibrillation shock from an AICD, the diffusion layer could be relatively thick and the rate of recovery would be relatively slow. Fluid flow of the electrolyte solution causes convective transport of reactive species from the bulk to the outer portions of the diffusion layer, effectively reducing the thickness of the diffusion layer and resulting in faster equilibration of the concentration of the species at the electrode-to-electrolyte interface with that of the bulk. That phenomenon has been exploited in the present invention.

In addition to the above phenomenon, we describe below another phenomenon that may underlie our discovery and that may be useful, either in addition to or as an alternative to the above phenomenon, in understanding the invention. We have observed that the delivery of high energy defibrillation shocks, e.g., 700 Volts., 42 Joules, between electrodes disposed in a saline solution results in the generation of gas micro-bubbles at the electrodes, which we believe to be oxygen and/or hydrogen gas liberated by hydrolysis. A portion of the bubbles has been observed to adhere to the surface of the electrodes after delivery of the shock, and to disappear, presumably by dissolution, over time. Assuming that such bubbles are also generated at defibrillating electrodes disposed in contact with blood, which we have not verified due to the opacity of whole blood, it is possible that such bubbles play a role in the discrimination of blood flow in the present invention, either in addition to the electrochemical explanation set forth above, or as an alternative explanation. It is reasonable to assume that bubbles adhered to the surface of the electrode would affect the electrical characteristics of the electrode by adding resistive and/or capacitive effects, and that the flow of blood past the electrode would cause the bubbles to dissipate more readily by dislodging them or enhancing dissolution, or both, resulting in a sudden change in the rate of decay of the residual potential of the electrode.

The principle of operation of the invention involves imposing a potential difference between first and second electrodes, at least one of which (referred to herein as the first electrode) is located in a blood flow path of the cardiovascular system, measuring a change in the potential difference between the first electrode and a reference electrode as a function of time during an unknown flow condition, and comparing the function measured during an unknown flow condition with a reference function representing a known flow condition. The results of the comparison are used either qualitatively to discern flow or non-flow, or quantitatively to discern flow velocity and/or flow rate. The first and reference electrodes both can be conventional stimulation electrodes, or the first electrode can be a conventional stimulation electrode and the reference electrode can be a conventional sensing electrode or an indifferent electrode. Electrodes dedicated only to flow discrimination can also be used, if desired.

Figure 3:
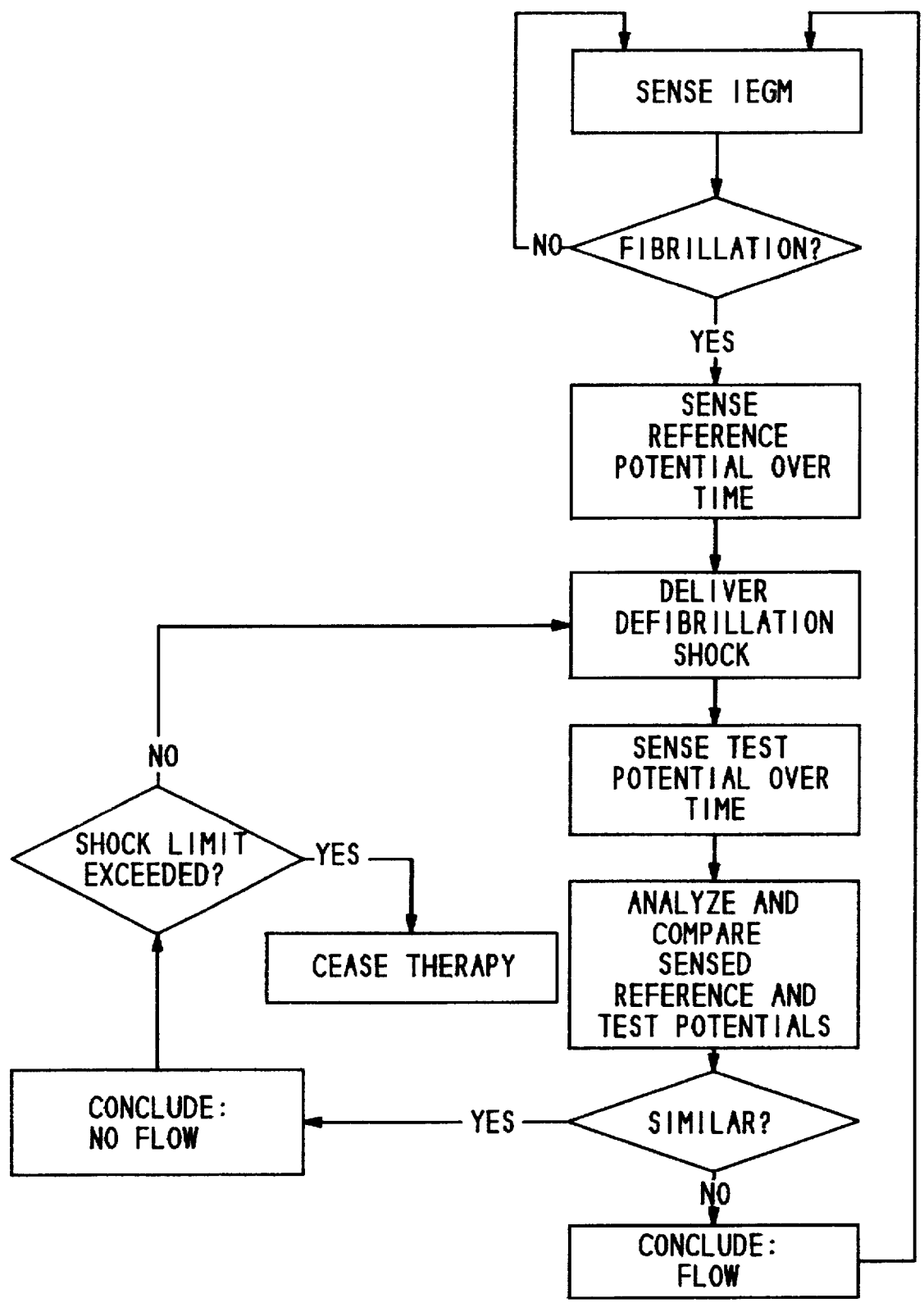
FIG. 3 is a flow chart of one mode of operation of the present invention.

Referring to FIG. 3, there is shown a flow chart illustrating one mode of operation of the present invention. That mode involves imposing an electrical potential between the first electrode and a second electrode during a known, or assumed, condition of non-flow of the blood, so that a potential equilibration function can be established as a basis for comparison. Such an electrical potential can be imposed by a reference shock delivered by an AICD between its defibrillation electrodes (one of which is defined as the first electrode herein) after having diagnosed fibrillation by conventional means, such as by conventional analysis of the IEGM. With fibrillation having been diagnosed, it is assumed that blood is not flowing at the time that the reference shock is delivered. Following delivery of the reference shock, a reference potential equilibration function is measured between the first electrode and a reference electrode. To insure that a reference potential equilibration function is measured that is representative of a non-flow condition, it is preferred that the energy delivered by the reference shock be sufficiently low to be unlikely to cause defibrillation, and yet be sufficiently high to generate an overvoltage that is easily measured between the first and reference electrodes. Following delivery of a subsequent defibrillation shock having an energy level that is expected to be effective to defibrillate the heart, a test potential equilibration function is measured between the first and reference electrodes. The reference and test potential equilibration functions are then analyzed and compared to each other. If the reference and test potential equilibration functions are sufficiently similar with regard to certain defining parameters, it can be concluded that a condition of non-flow remains after delivery of the defibrillation shock and that further defibrillation therapy is necessary. If the reference and test potential equilibration functions are sufficiently different with regard to certain defining parameters, it can be concluded that blood flow has resumed and that the heart has been successfully defibrillated, and that defibrillation therapy can be discontinued. In the event that a further defibrillation shock is deemed necessary, a further test potential equilibration function is measured subsequent thereto and compared with the reference measured potential equilibration function to determine whether the further shock was successful in defibrillating the heart. The process can be continued for subsequent shocks if necessary, provided that a preprogrammed limit of the number of permissible shocks is not exceeded.

The mode of operation described above can be generalized to permit discrimination of flow of blood in a cardiovascular system without requiring integration with defibrillation therapy. For example, the reference shock can be delivered between the first and second electrodes at a time when the state of flow of blood at the first electrode is known or unknown, with the state of flow not necessarily being one of non-flow, and/or without having previously diagnosed fibrillation by other means. The subsequent shock can be generalized as a test shock, not necessarily having a defibrillating purpose. Comparison of the reference and test potential equilibration functions yields the state of flow of blood following delivery of the test shock relative to the state of flow at the time of delivery of the reference shock.

The mode of operation of the invention can be further generalized by eliminating the initial reference shock and proceeding directly to delivery of a test shock at a time when the state of flow of blood is unknown. The test potential equilibration function can then be compared to a predefined reference function representing a known flow condition to discriminate the state of flow at the time of the test shock.

The relative similarity or difference between the reference and test potential equilibration functions can be determined by applying algorithms involving, for example, regression analysis, discrete numerical differentiation, or real-time signal processing. Where the potential equilibration function is represented by f(t), the first derivative $f'(t)=\partial V/\partial t$ and/or the second derivative $f''(t)=\partial^2 V/\partial t^2$ can be used to discern differences of slope or change of slope to discriminate flow. Algorithms involving regression analysis that may be used to determine differences between the pre- and post-shock potential equilibration functions include, for example, comparison of the damping constant, $\alpha$, where the potential equilibration function is represented by $f(t)=Ae^{\pm\alpha t}$, where A is an amplitude constant and e is the base of the natural logarithm, and comparison of one or more of the polynomial coefficients, $a_j$, where the potential equilibration function is represented by f(t), and a general polynomial fit of degree n is expressed as $\Sigma_{j=0}^{n} a_j t^j$.

The ability of the present invention to discriminate between flow and non-flow conditions in the post-shock period is believed to be enhanced as the number of successive therapeutic shocks increases, whereas conventional techniques that analyze IEGM signals may become less reliable. IEGM analysis involves detecting a series of small amplitude pulses generated by the electrical activity of the myocardium. In some situations, the series of pulses weakens progressively in amplitude following repeated therapeutic shocks so that the AICD may fail to discern ventricular depolarization and repolarization, and continue to deliver shock therapies after fibrillation has been terminated. With regard to the present invention, repeated shocks are believed to lead to a greater concentration gradient between the electrode/electrolyte interface and the bulk of the electrolyte. Thus, when fibrillation is terminated and flow starts, a dramatic change in the potential equilibration function occurs, enhancing detection. Thus, the present invention helps prevent the patient from receiving unnecessary shocks.

It is believed that the principles underlying the present invention can be exploited with any two electrodes having access to an ionically conductive path in the body, with at least one of the electrodes in a blood flow path, provided that the blood-contacting electrode develops an overvoltage upon application of an electrical potential. Both electrodes could be located in contact with blood in a blood flow path of the cardiovascular system, such as in a ventricle or atrium, or superior vena cava, or one electrode could be located subcutaneously, at the AICD housing for example, or pericardially. Electrode materials that are believed to be suitable for use as the first and reference electrodes include: titanium, titanium coated with iridium oxide, platinum, platinum-iridium alloy, titanium nitride, carbon, coatings or composites of the above materials, and other polarizable electrode materials. Electrode materials that are also believed to be suitable for the reference electrode include calomel, silver/silver chloride, and other non-polarizing electrode materials. Where the reference electrode is also the second electrode relative to which the potential of the first electrode is applied, it is believed that only polarizable electrode materials should be used for the reference electrode.

Figure 4:
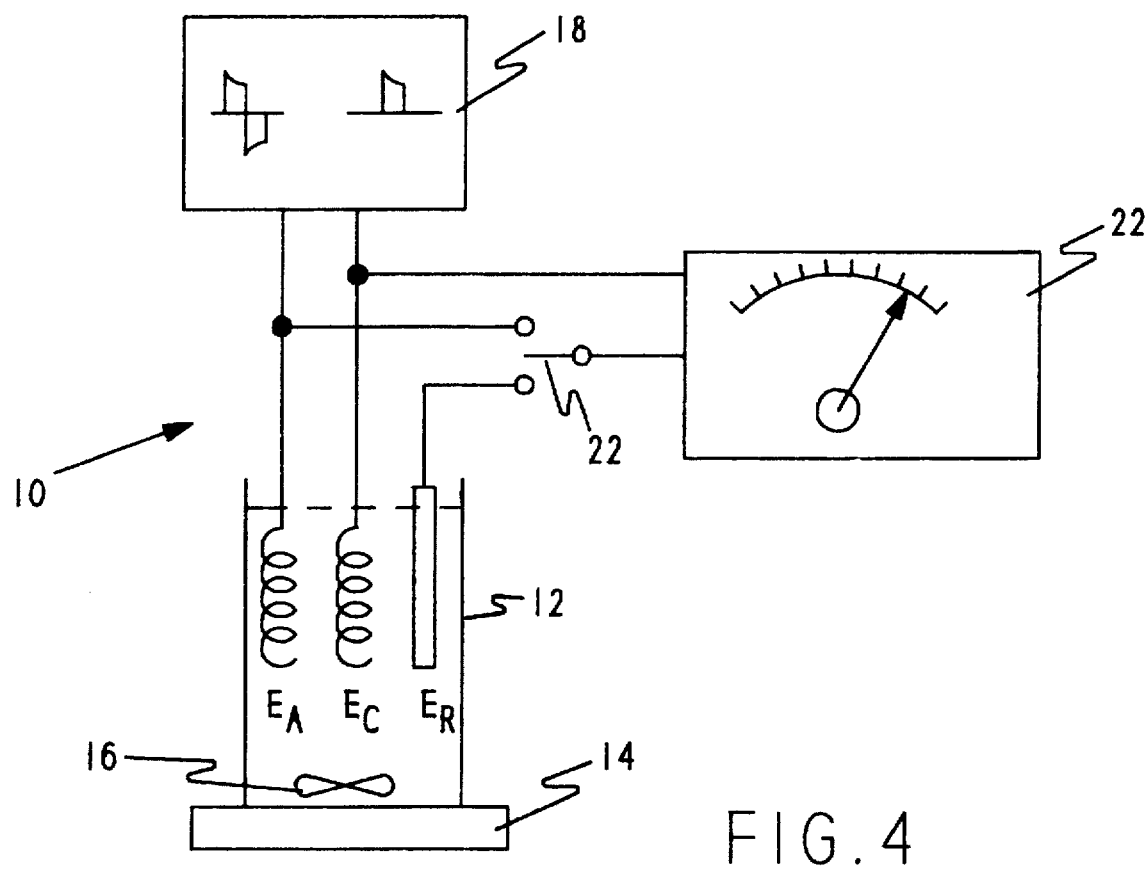
FIG. 4 is an experimental setup useful for demonstrating some aspects of the present invention.

Referring to FIG. 4, there is illustrated in schematic form an experimental setup 10 that was used to gather in vitro data to demonstrate certain aspects of the present invention. The setup 10 includes a beaker 12 holding an electrolyte solution, a magnetic stirrer 14 supporting beaker 12, a teflon-coated stir bar 16 located in the electrolyte solution inside the beaker 12, three electrodes labeled $E_A$ (anode), $E_C$ (cathode) and $E_R$ (reference), a shock generator 18, a single-pole double-throw switch 20, and a potential recorder 22. Various electrolyte solutions were used, including, for example: a 50/50 (percent by volume) mixture of normal saline solution and Ringers lactate solution; a 50/50 (percent by volume) mixture of canine and equine blood plasma; and 100% canine blood. Various electrode materials were used, including: titanium coils for both anode and cathode; and iridium oxide coated titanium coils for both anode and cathode. In some cases, the anode $E_A$ was used as a reference electrode; in other cases, titanium or calomel electrodes were used for the reference electrode $E_R$.

The experimental procedure involved applying either a bi-phasic or a monophasic transient shock from shock generator 18 between the cathode $E_C$ and the anode $E_A$ immersed in the electrolyte. The potential between cathode $E_C$ and either anode $E_A$ or reference electrode $E_R$, as selected by switch 20, was then measured by potential recorder 22. Data for non-stirred (quiescent) electrolyte were collected first, followed by data for stirred electrolyte. In the stirred case, the magnetic stirrer was turned on after delivery of the shock, to simulate the effect of defibrillation and resumption of cardiac output.

| Example 1 | |
|---|---|
| Shock electrodes: | Titanium coil cathode |
|  | Titanium coil anode |
| Sensing electrode: | Cathode |
| Reference electrode: | Anode |
| Electrolyte: | Saline/Ringers lactate; |
|  | impedance @ 50 kHz = 35 ohms |
| Shock: | Monophasic, 700 V, 42 Joules |

Figure 5:
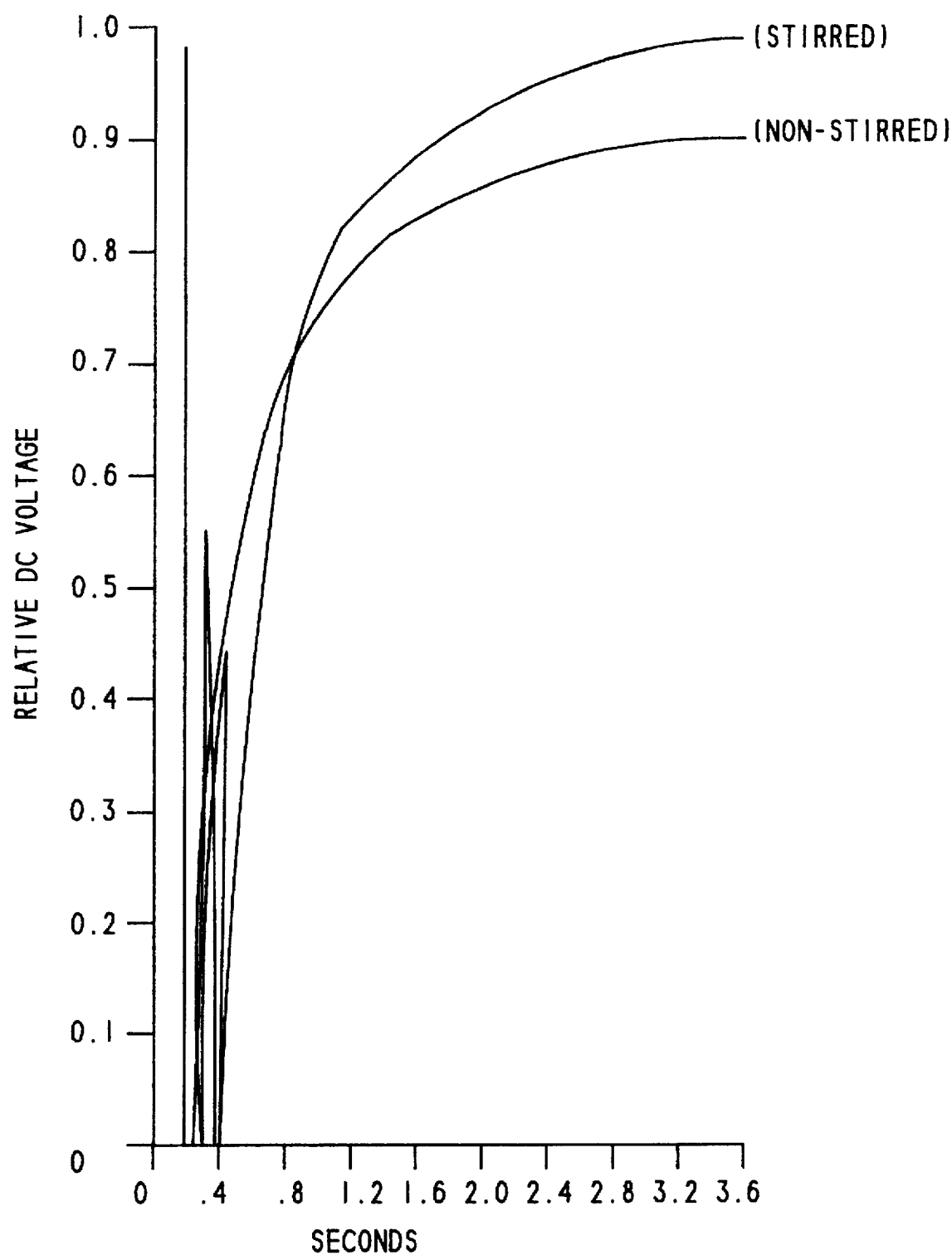
FIGS. 5–10 are potential curves plotted as a function of time, corresponding to Examples 1–6 in the text, respectively.

Referring to FIG. 5, potential equilibration functions are shown for non-stirred and stirred electrolyte, as measured between the cathode and anode following a 700 V. monophasic shock between the cathode and anode. It can be observed that the potential equilibration function has a greater average slope in the stirred case than in the non-stirred case. The stirred and non-stirred potential equilibration functions shown in FIG. 5 can be compared and analyzed by establishing a best-fit first-order polynomial for each function. The best-fit line for the non-stirred equilibration function has a slope of $2.29 \times 10^{-03}$. The best-fit line for the stirred equilibration function has a slope of $3.44 \times 10^{-03}$. The slope in the stirred case is approximately 50% greater than the slope in the non-stirred case. This difference is sufficiently great to be distinguishable by an AICD using a detection algorithm based upon the slope of the measured equilibration function.

| Example 2 | |
|---|---|
| Shock electrodes: | Titanium coil coated with iridium oxide, cathode |
|  | Titanium coil coated with iridium oxide, anode |
| Sensing electrode: | Cathode |
| Reference electrode: | Calomel |
| Electrolyte: | Saline/Ringers lactate; |
|  | impedance @ 50 kHz = 33 ohms |
| Shock: | Monophasic, 700 V, 42 Joules |

Figure 6:
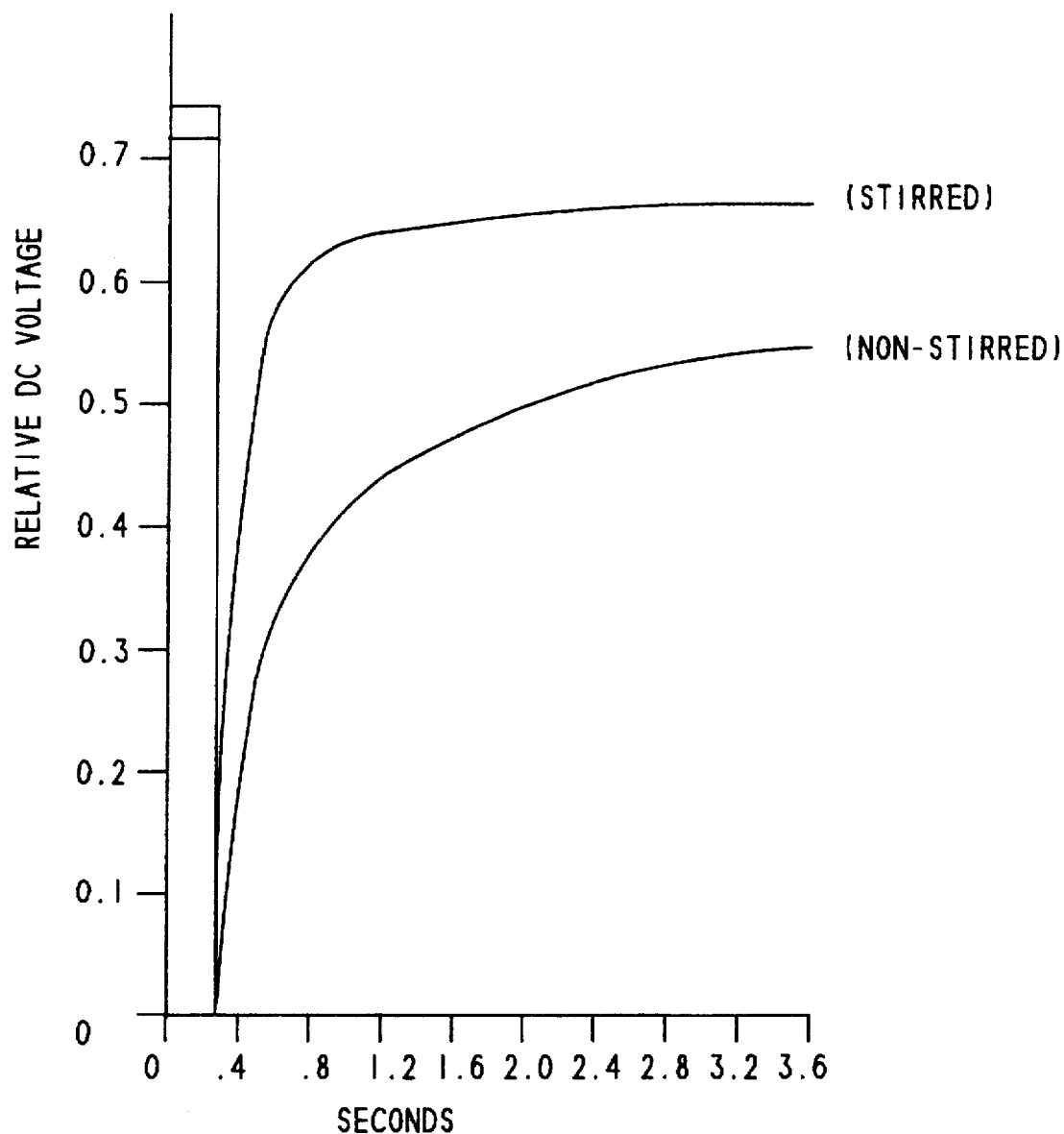

Referring to FIG. 6, potential equilibration functions are shown for non-stirred and stirred electrolyte, as measured between the cathode and the calomel reference electrode following a 700 V. monophasic shock between the cathode and anode. The stirred and non-stirred potential equilibration functions shown in FIG. 6 can be compared and analyzed by establishing a best-fit third-order polynomial for each function. The second-order coefficient, $a_2$, is $1.19 \times 10^{-04}$ for the non-stirred case, whereas the second-order coefficient is $1.91 \times 10^{-05}$ for the stirred case. The difference between the values of the second-order coefficients is 623%, which is sufficiently great to be distinguishable by an AICD using a detection algorithm based upon a best-fit third-order polynomial.

| Example 3 | |
|---|---|
| Shock electrodes: | Titanium coil coated with iridium oxide, cathode |
|  | Titanium coil coated with iridium oxide, anode |
| Sensing electrode: | Cathode |
| Reference electrode: | Calomel |
| Electrolyte: | Canine/equine plasma, 50/50% by volume; |
|  | impedance @ 50 kHz = 18 ohms |
| Shock: | Monophasic, 700 V, 45 Joules |

Figure 7:
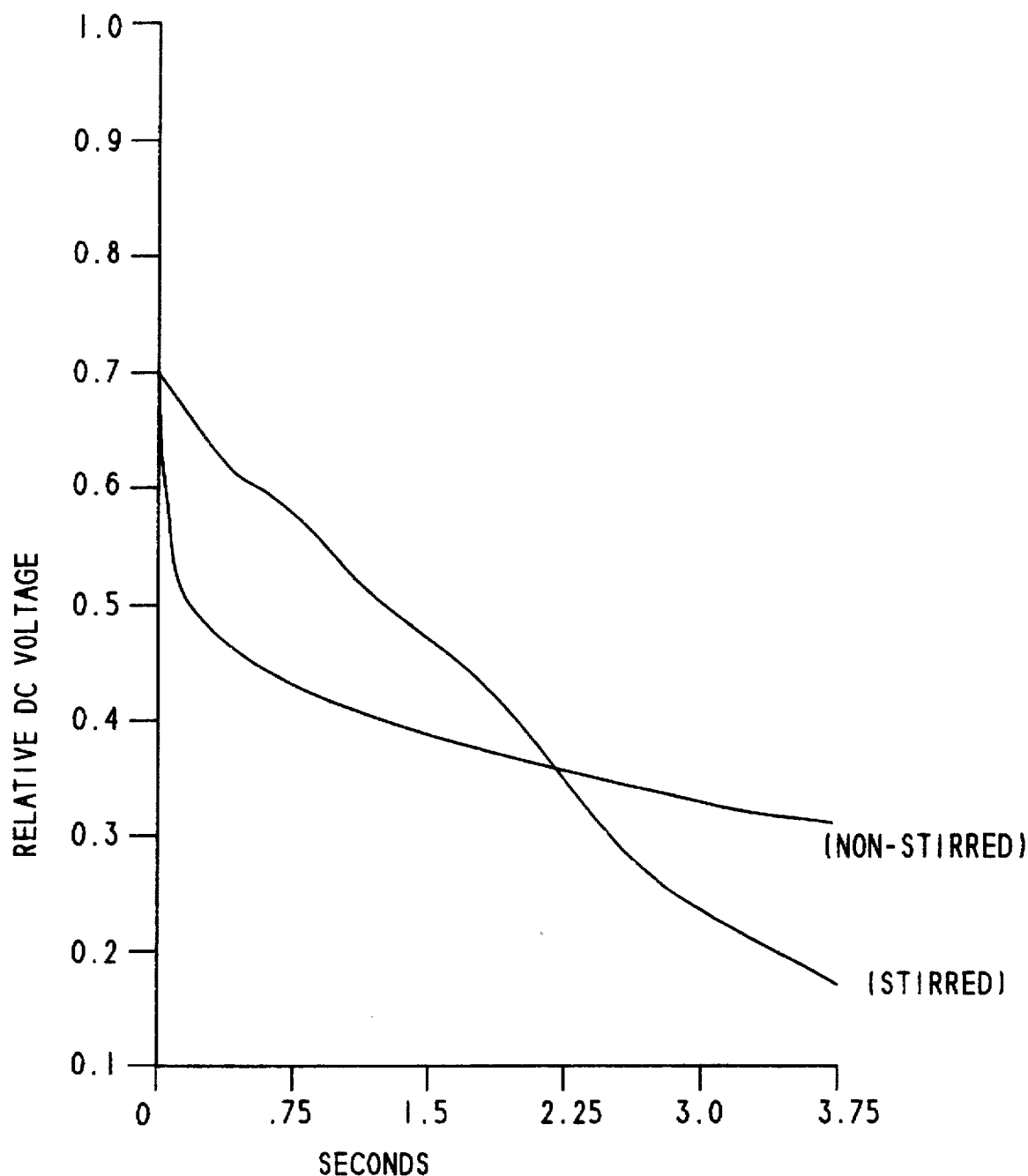

Referring to FIG. 7, potential equilibration functions are shown for non-stirred and stirred electrolyte, as measured between the cathode and the calomel reference electrode following a 700 V. monophasic shock between the cathode and anode. The curves are inverted relative to the previous examples due to the choice of polarity assigned to the potential recorder leads. It can be observed that the potential equilibration function for the stirred case has an inflection point at which $\partial^2 V/\partial t^2 = 0$ at the beginning of stirring (flow). Also, the stirred and non-stirred potential equilibration functions shown in FIG. 7 can be compared and analyzed by establishing a best-fit third-order polynomial for each function. The second-order coefficient, $a_2$, is $-7.2 \times 10^{-05}$ for the non-stirred case, whereas the second-order coefficient, $a_2$, is $12.2 \times 10^{-05}$ for the stirred case. The difference between the absolute value of the coefficients is 69%, which is sufficiently great to be distinguishable by an AICD using a detection algorithm based upon a best-fit third-order polynomial.

| Example 4 | |
|---|---|
| Shock electrodes: | Titanium coil, cathode |
|  | Titanium coil, anode |
| Sensing electrode: | Cathode |
| Reference electrode: | Titanium reference |
| Electrolyte: | Canine/equine plasma, 50/50% by volume; |
|  | impedance @ 50 kHz = 18 ohms |
| Shock: | Monophasic, 700 V, 45 Joules |

Figure 8:
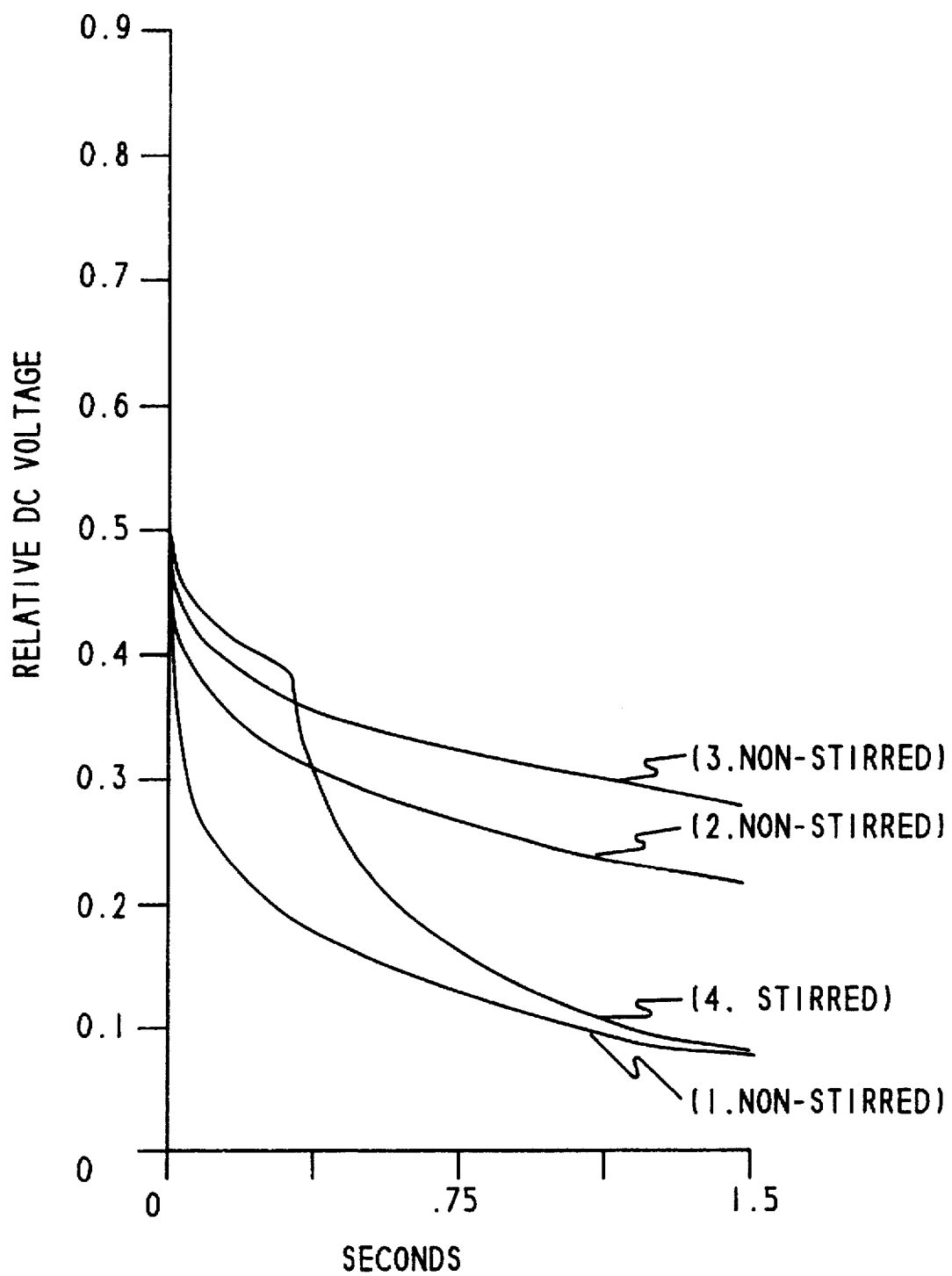

Referring to FIG. 8, potential equilibration functions are shown for four successive shocks, each separated in time by ten seconds and delivered in the order indicated in parentheses next to each curve, as measured between the cathode and a titanium reference electrode following a 700 V. monophasic shock between the cathode and anode. The first three shocks were delivered with non-stirred electrolyte, and stirring was started subsequent to delivery of the fourth shock. It can be observed that the potential equilibration function for the stirred case has an inflection point at which $\partial^2 V/\partial t^2 = 0$ at the beginning of stirring (flow). Also, the stirred and non-stirred potential equilibration functions shown in FIG. 8 can be compared and analyzed by establishing a best-fit third-order polynomial for each function. The first-order coefficient for the first three (non-stirred) equilibration functions is $-3.85 \times 10^{-06} \pm 5\%$. After stirring commences, with regard to the fourth equilibration function, the first-order coefficient is $-966 \times 10^{-06}$, a difference of about 390%. In terms of signal amplitude, the difference is on the order of 6 dB, which is sufficiently great to be distinguishable by sense amplifiers in an AICD using a detection algorithm based upon a best-fit third-order polynomial.

| Example 5 | |
|---|---|
| Shock electrodes: | Titanium coil coated with iridium oxide, cathode |
| | Titanium coil coated with iridium oxide, anode |
| Sensing electrode: | Cathode |
| Reference electrode: | Anode |
| Electrolyte: | Canine blood; impedance @ 50 kHz = 35 ohms |
| Shock: | Monophasic, 200 V, 4 Joules |

Figure 9:
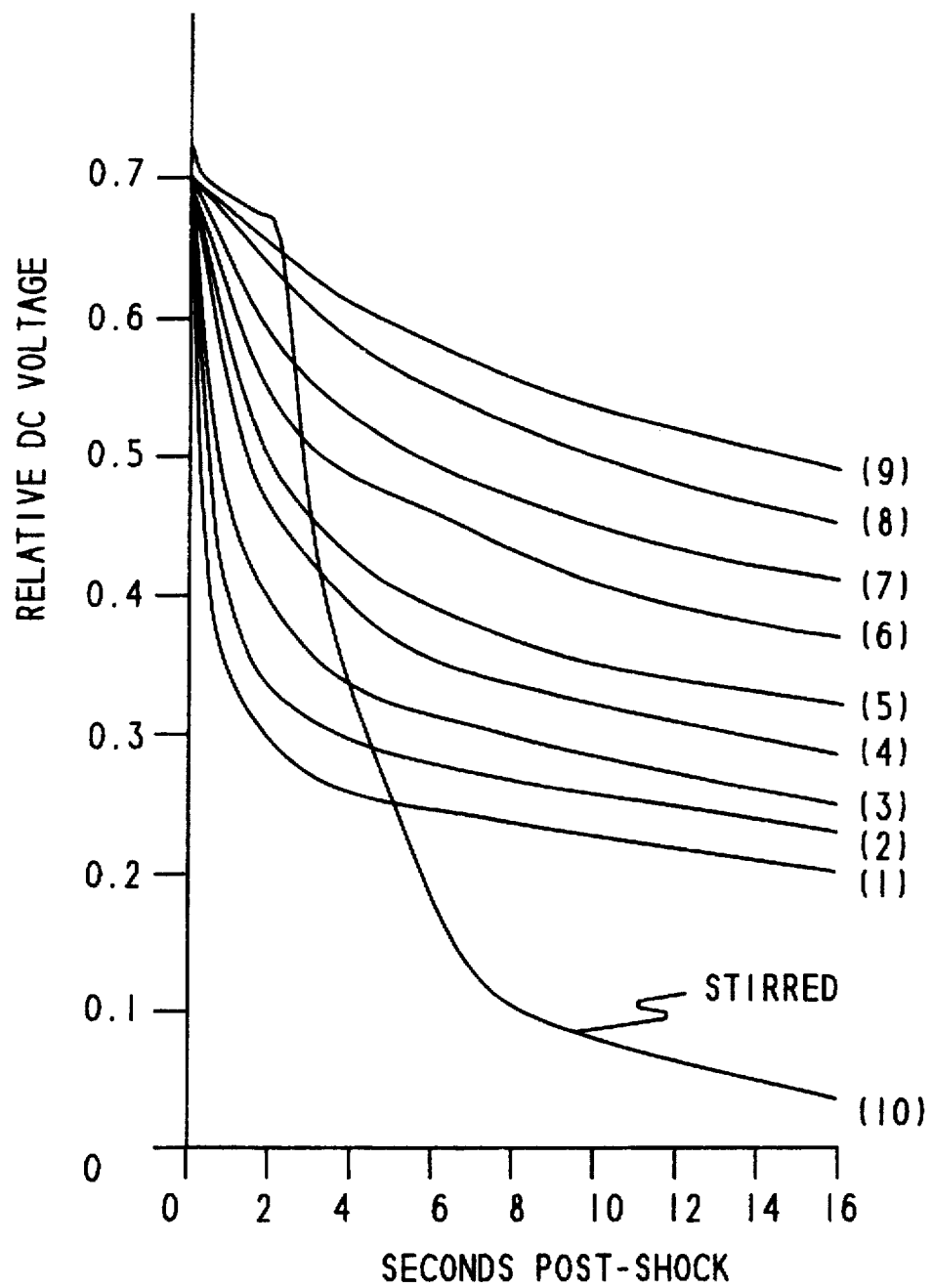

Referring to FIG. 9, potential equilibration functions are shown for ten successive shocks, each separated in time by fifteen seconds and delivered in the order indicated in parentheses next to each curve, as measured between the cathode and anode following a 200 V. monophasic shock between the cathode and anode. The first nine shocks were delivered with non-stirred electrolyte, and stirring was started subsequent to delivery of the tenth shock. It can be observed that the potential equilibration function for the stirred case has an inflection point at which $\partial^2 V/\partial t^2 = 0$ at the beginning of stirring (flow). Also, the stirred and non-stirred potential equilibration functions shown in FIG. 9 can be compared and analyzed by establishing a best-fit third-order polynomial for each function. The second-order coefficient for the first nine (non-stirred) equilibration functions is $24 \times 10^{-06} \pm 5\%$. After stirring commences, with regard to the tenth equilibration function, the second-order coefficient is $5.67 \times 10^{-06}$, a difference of about 423%. In terms of signal amplitude, the difference is on the order of 6 dB, which is sufficiently great to be distinguishable by sense amplifiers in an AICD using a detection algorithm based upon a best-fit third-order polynomial.

EXAMPLE 6

Another experimental procedure involved in vivo demonstration in a dog of some aspects of the present invention. In that procedure, the shock electrodes were a titanium coil affixed in the right ventricle of the heart in a blood flow path, and a titanium mesh patch implanted subcutaneously. The reference electrode was a titanium housing, or can, of the type used to enclose an implantable cardiac stimulator, implanted pectorally. The electrolyte was, of course, canine blood, with an impedance of 62 ohms measured at 50 kHz between the shock electrodes. The shock was bi-phasic, delivered at two different energy levels: 200 V, 4 Joules; and 400 V, 49 Joules.

Figure 10:
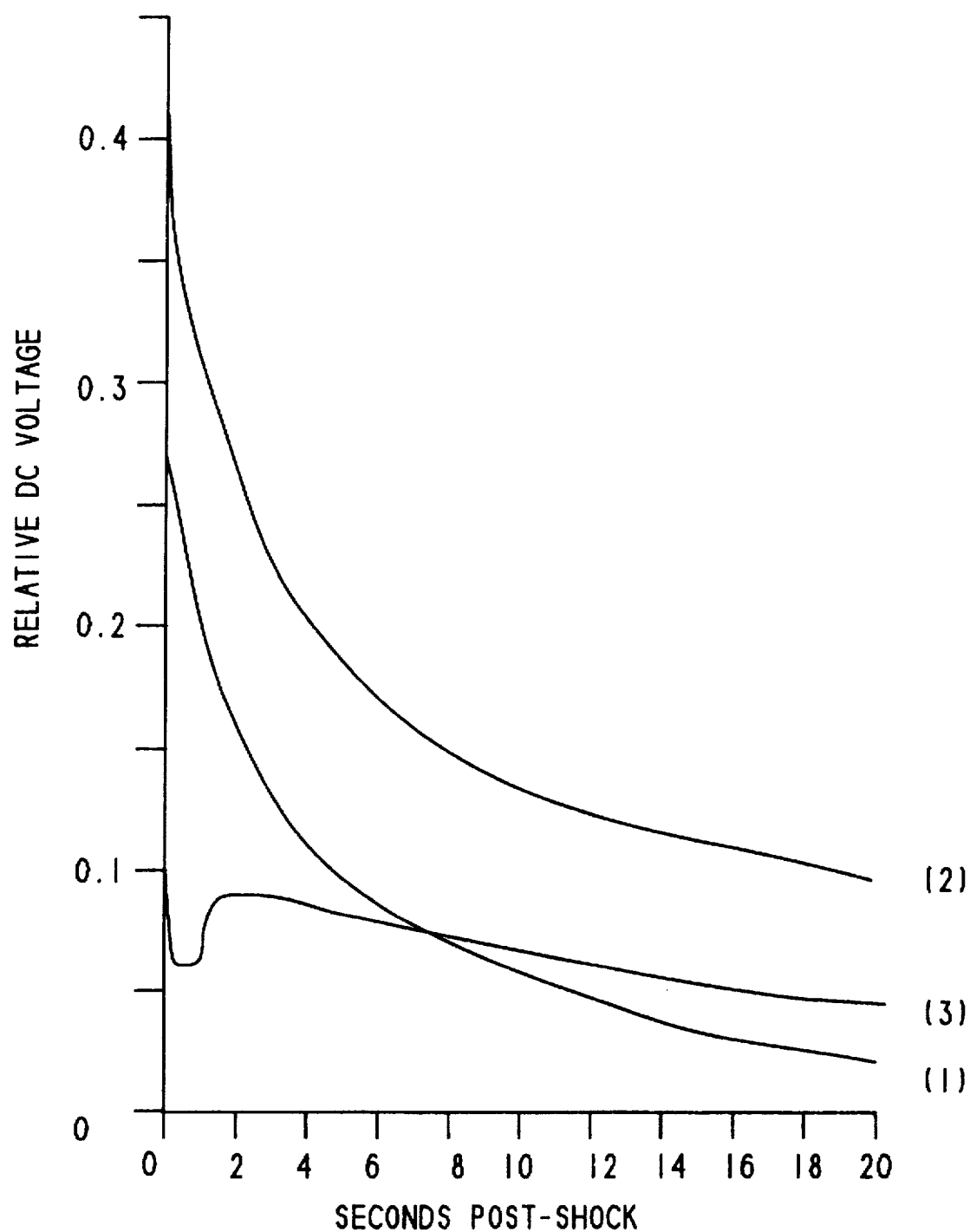

Referring to FIG. 10, potential equilibration functions are shown for three successive bi-phasic shocks. Fibrillation was induced, after which each shock was delivered between the right ventricular electrode and the subcutaneous patch electrode in the order shown by the numbers in parentheses next to each curve. The potential equilibration functions were measured, subsequent to each shock, between the right ventricular electrode and the subcutaneous pectoral electrode. The first two shocks were at 200 V, 4 Joules, and failed to defibrillate. The third shock was at 700 V, 49 Joules, and successfully restored normal cardiac rhythm and cardiac output. The potential equilibration functions shown in FIG. 10 can be compared and analyzed by establishing a best-fit fourth-order polynomial for each function. The fourth-order coefficient, $a_4$, for the first two (fibrillation, no blood flow) equilibration functions is on the order of $3 \times 10^{-12}$, whereas the similarly derived fourth-order coefficient for the third (defibrillation, cardiac output) equilibration function is on the order of $-900 \times 10^{-015}$. The difference between the absolute values of the coefficients is about 333%, which is sufficiently great to be distinguishable by sense amplifiers in an AICD using a detection algorithm based upon a best-fit fourth-order polynomial.

Figure 11:
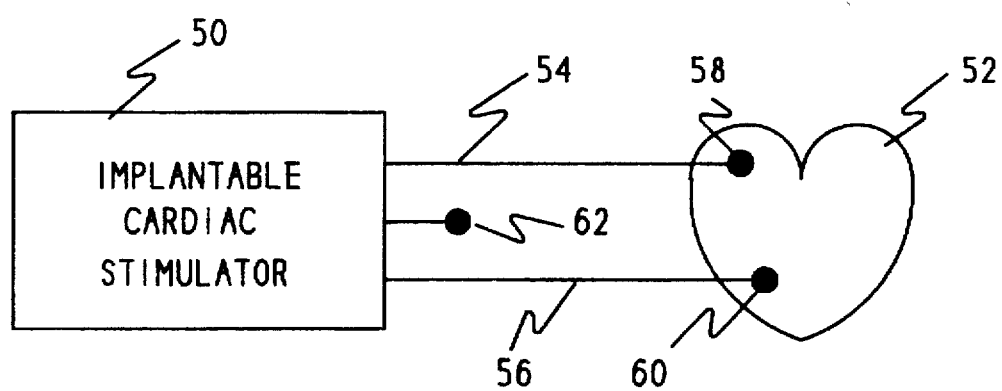
FIG. 11 is a block diagram of an implantable cardiac stimulator in accordance with the present invention.

Referring to FIG. 11, there is illustrated in block form an implantable cardiac stimulator 50, preferably an automatic implantable cardioverter/defibrillator, incorporating conventional means for sensing a condition of fibrillation and for delivering stimulating shocks as described above, and incorporating means for performing the measurements and comparisons, described above, for discriminating flow of blood following delivery of a therapeutic shock. The stimulating and sensing electrodes described below with respect to FIG. 11 will be understood as corresponding to the first, second and reference electrodes described above in connection with the general description of the principles of the invention. Stimulator 50 is electrically connected to heart 52 via conductive insulated leads 54 and 56, terminating in stimulating electrodes 58 and 60, respectively, at least one of which is located in a blood flow path of the cardiovascular system. A third electrode 62 can be embodied as the conductive housing, or can, of stimulator 50, or can be located remotely from stimulator 50 subcutaneously, or in the superior vena cava, or other location within the body so long as there is an ionically conductive path between electrode 62 and the stimulating electrode located in the blood flow path. At least one of the pair of stimulating electrodes 58 and 60 must be in contact with blood in a blood flow path of the cardiovascular system to function as the first electrode. One of the other electrodes can then function as the second and/or reference electrodes.

Figure 12:
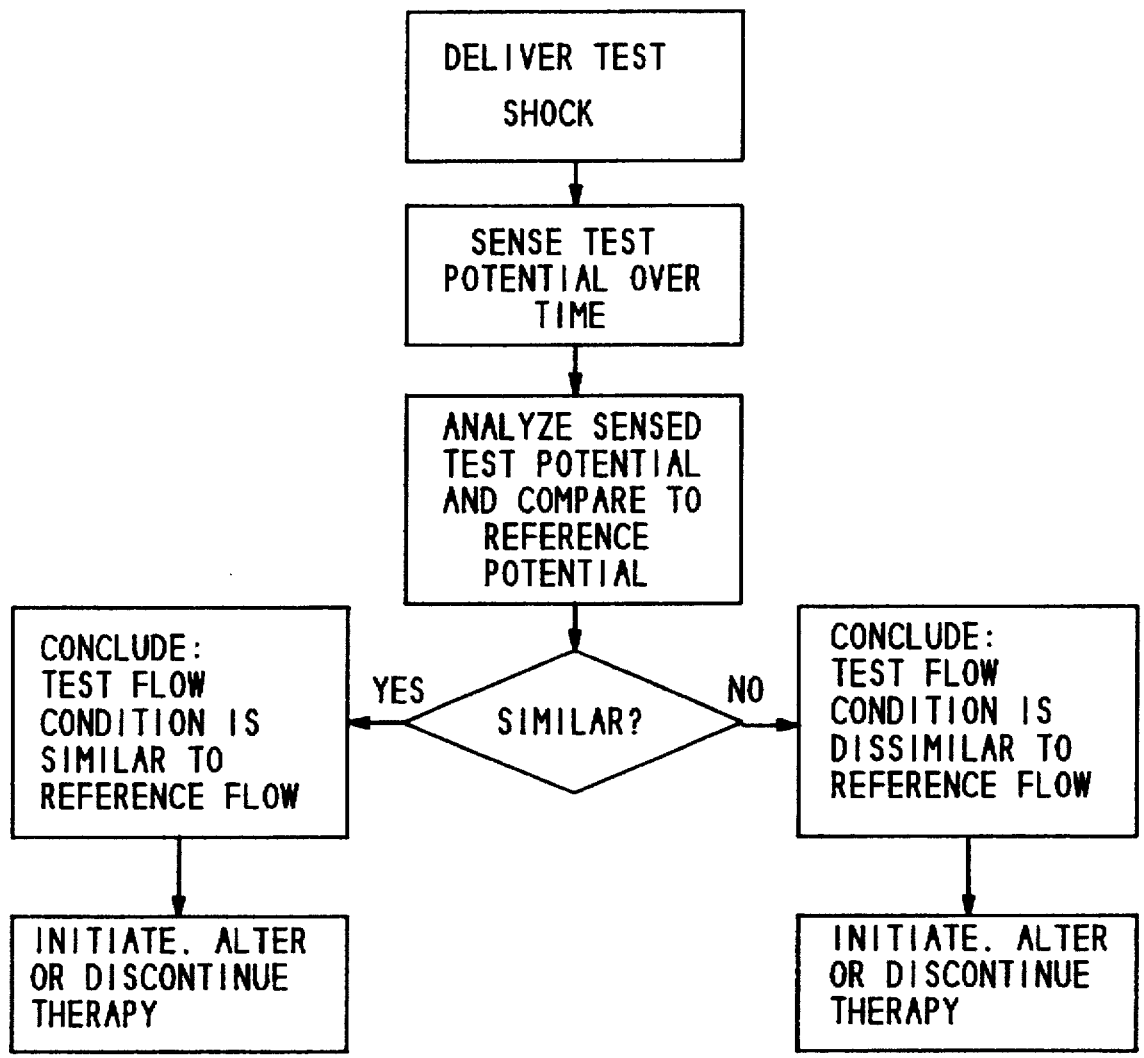
FIG. 12 is a flow chart of another mode of operation of the present invention.

Referring to FIG. 12, there is shown a flow chart illustrating another mode of operation of the present invention. That mode involves imposing an electrical potential between the first electrode and a second electrode during an unknown flow condition of the blood. Such an electrical potential can be imposed by a test shock delivered by an AICD between its defibrillation electrodes, one of which is defined as the first electrode herein. Following delivery of the test shock, a test potential equilibration function is measured between the first electrode and a reference electrode. The test potential equilibration function is then analyzed and compared to a reference potential equilibration function representing a known flow condition. If the reference and test potential equilibration functions are sufficiently similar with regard to certain defining parameters, it can be concluded that the unknown flow condition is qualitatively or quantitatively similar to the flow condition represented by the reference potential equilibration function. If the reference and test potential equilibration functions are sufficiently different with regard to certain defining parameters, it can be concluded that the unknown flow condition is qualitatively or quantitatively dissimilar to the flow condition represented by the reference potential equilibration function. With the unknown flow condition having been characterized relative to a reference flow condition, the AICD can assess the hemodynamic condition of the patient and initiate, alter, or cease delivery of therapy, as may be appropriate. Thus, the present invention can be used as a primary sensor to diagnose hemodynamically unstable cardiac arrhythmias, in addition to being used as a supplemental or secondary sensor in combination with IEGM sensing.

While the present invention has been illustrated and described with particularity in terms of a preferred method and preferred embodiments, it should be understood that no limitation of the scope of the invention is intended thereby. The scope of the invention is defined only by the claims appended hereto. It should also be understood that variations of the particular embodiments described herein incorporating the principles of the present invention will occur to those of ordinary skill in the art and yet be within the scope of the appended claims.

We claim:

1. An implantable cardiac stimulator, comprising:

a first implantable electrode configured for implanting in a blood flow path of the cardiovascular system of a body;

a second implantable electrode configured for implanting in the body such that an ionically conductive path exists through the body between the first and second electrodes;

a reference implantable electrode configured for implanting in the body such that an ionically conductive path exists through the body between the first and reference electrodes;

means for detecting cardiac fibrillation, whereby, if fibrillation is detected, a state of substantially no flow of blood at said first electrode can be assumed;

means in electrical communication with said first and second electrodes for delivering a reference shock between said first and second electrodes at a time when there is substantially no flow of blood at said first electrode, and for subsequently delivering a defibrillation shock between said first and second electrodes;

means for sensing in the time domain a reference electrical potential between said first electrode and said reference electrode following delivery of said reference shock, and for sensing in the time domain a test electrical potential between said first electrode and said reference electrode following delivery of said defibrillation shock; and means for analyzing and comparing said sensed reference electrical potential and said sensed test electrical potential, and for determining on the basis of said comparison whether blood is flowing following delivery of said defibrillation shock.

2. The implantable cardiac stimulator of claim 1, in which said second electrode and said reference electrode are electrically common at a common locus.

3. The implantable cardiac stimulator of claim 1, in which said second electrode and said reference electrode are electrically non-common at separate loci.

4. The implantable cardiac stimulator of claim 1, in which said means for analyzing and comparing includes means for performing a regression analysis of each of said sensed reference and test electrical potentials.

5. The implantable cardiac stimulator of claim 4, in which said regression analysis includes determining a damping constant, $\alpha$, where the sensed reference and test electrical potentials are expressed as a function of time by the equation $f(t)=Ae^{\pm \alpha t}$, in which A is a constant, e is the base of the natural logarithm, and t is time, and comparing the damping constants of said sensed reference and test electrical potentials.

6. The implantable cardiac stimulator of claim 4, in which said regression analysis includes determining a coefficient, a, where the sensed reference and test electrical potentials are expressed as a function of time by the equation $$f(t) = \sum_{j=0}^{n} a_j t^j, \text{ where } t \text{ is time,}$$

representing a general polynomial fit of degree n, and comparing the coefficients of said sensed reference and test electrical potentials.

7. The implantable cardiac stimulator of claim 1, in which said means for analyzing and comparing includes means for performing differentiation of the sensed reference and test electrical potentials, and, given that the first derivative of the sensed reference and test electrical potential is expressed as a function of time by the equation $f'(t)=\partial V/\partial t$, in which V is the sensed electrical potential and t is time, comparing the values of f'(t) for said reference and test electrical potentials.

8. The implantable cardiac stimulator of claim 1, in which said means for analyzing and comparing includes means for performing differentiation of the sensed reference and test electrical potentials, and, given that the second derivative of the sensed reference and test electrical potentials are expressed as a function of time by the equation $f''(t)=\partial^2 V/\partial t^2$, in which V is the sensed electrical potential and t is time, comparing the values of f''(t) for said reference and test electrical potentials.

9. The implantable cardiac stimulator of claim 1, in which said means for analyzing and comparing includes signal processing means for processing said sensed reference and test electrical potentials to generate the first derivative of each of said potentials, and comparing the values of the first derivative for said reference and test electrical potentials.

10. The implantable cardiac stimulator of claim 1, in which said means for analyzing and comparing includes signal processing means for processing said sensed reference and test electrical potentials to generate the second derivative of each of said potentials, and comparing the values of the second derivative for said reference and test electrical potentials.

11. A method for discriminating cardiovascular blood flow, comprising the steps of:

implanting a first electrode in a blood flow path of the cardiovascular system;

implanting a second electrode such that an ionically conductive path exists between said first and second electrodes;

implanting a reference electrode such that an ionically conductive path exists between said first and reference electrodes;

detecting cardiac fibrillation, whereby, if fibrillation is detected, a state of substantially no flow of blood at said first electrode can be assumed;

delivering a reference electrical shock between said first and second electrodes at a time when there is substantially no flow of blood at said first electrode;

subsequently delivering a defibrillating electrical shock between said first and second electrodes;

sensing in the time domain a reference electrical potential between said first and reference electrodes following delivery of said reference electrical shock;

sensing in the time domain a test electrical potential between said first and reference electrodes following delivery of said defibrillation electrical shock;

analyzing and comparing said test electrical potential to said reference electrical potential, and determining, on the basis of said comparison, whether blood is flowing following delivery of said defibrillation electrical shock.

12. The method of claim 11, in which said step of implanting a second electrode and said step of implanting a reference electrode are performed commonly by implanting a common component comprising both said second electrode and said reference electrode.

13. The method of claim 11, in which said step of implanting a second electrode and said step of implanting a reference electrode are performed independently by implanting separate components comprising said second and reference electrodes, respectively.

14. The method of claim 11, in which said step of analyzing and comparing includes performing a regression analysis of each of said sensed reference and test electrical potentials.

15. The method of claim 14, in which said regression analysis includes determining a damping constant, $\alpha$, where the sensed reference and test electrical potentials are expressed as a function of time by the equation $f(t)=Ae^{\pm\alpha t}$, in which A is a constant, e is the base of the natural logarithm, and t is time, and comparing the damping constants of said sensed reference and test electrical potentials.

16. The method of claim 14, in which said regression analysis includes determining a coefficient, a, where the sensed reference and test electrical potentials are expressed as a function of time by the equation $f(t)=\Sigma_{j=0}^{n} a_j t^j$, in which t is time, representing a general polynomial fit of degree n, and comparing the coefficients of said sensed reference and test electrical potentials.

17. The method of claim 11, in which said step of analyzing and comparing includes performing differentiation of the sensed reference and test electrical potentials, and, given that the first derivative of the sensed reference and test electrical potentials are expressed as a function of time by the equation $f'(t)=\partial V/\partial t$, in which V is the sensed electrical potential and t is time, comparing the values of f'(t) for said reference and test electrical potentials.

18. The method of claim 11, in which said step of analyzing and comparing includes performing differentiation of the sensed reference and test electrical potentials, and, given that the second derivative of the sensed reference and test electrical potentials are expressed as a function of time by the equation $f''(t)=\partial^2 V/\partial t^2$ in which V is the sensed electrical potentia and t is time, comparing the values of f''(t) for said reference and test electrical potentials.

19. The method of claim 11, in which said step of analyzing and comparing includes signal processing of said sensed reference and test electrical potentials to generate the first derivative of each of said potentials, and comparing the values of the first derivative for said reference and test electrical potentials.

20. The method of claim 11, in which said step of analyzing and comparing includes signal processing of said sensed reference and test electrical potentials to generate the second derivative of each of said potentials, and comparing the values of the second derivative for said reference and test electrical potentials.

21. A method of discriminating flow of blood in a cardiovascular system of a body, comprising the steps of:

disposing a first electrode in a blood flow path of the cardiovascular system;

disposing a second electrode such that an ionically conductive path exists through the body between said first electrode in a blood flow path and said second electrode, imposing an electrical potential on said first electrode by connecting a voltage source between said first electrode in the blood flow path and said second electrode;

disconnecting said voltage source from said first electrode after said electrical potential has been imposed;

allowing the electrical potential on said first electrode to discharge at least partially;

sensing the discharging electrical potential in the time domain following said step of imposing an electrical potential by disposing a reference electrode such that an ionically conductive path exists through the body between said first electrode in a blood flow path and said reference electrode, and sensing the potential of the electrode in a blood flow path relative to the potential of said reference electrode; and analyzing said sensed electrical potential to discriminate flow of blood, wherein said step of disposing a second electrode and said step of disposing a reference electrode are performed independently by implanting separate components comprising said second and reference electrodes, respectively.

22. An apparatus for discriminating flow of blood in a cardiovascular system, comprising:

a first implantable electrode configured for implanting in a blood flow path of the cardiovascular system;

a second implantable electrode configured for implanting in the body such that an ionically conductive path exists through the body between the first and second electrodes;

a reference implantable electrode configured for implanting in the body such that an ionically conductive path exists through the body between the first and reference electrodes in which said second electrode and said reference electrode are electrically non-common at separate locii;

means for sensing cardiac parameters from which the state of flow of blood at said first electrode can be deduced;

means in electrical communication with said first and second electrodes for delivering a reference shock between said first and second electrodes at a time when the state of flow of blood at said first electrode is known, and for subsequently delivering a test shock between said first and second electrodes;

means for sensing in the time domain a reference electrical potential between said first electrode and said reference electrode following delivery of said reference shock, and for sensing in the time domain a test electrical potential between said first electrode and said reference electrode following delivery of said test shock; and means for analyzing and comparing said sensed reference electrical potential and said sensed test electrical potential., and for determining on the basis of said comparison the state of flow of blood following delivery of said test shock.

* * * * *